United States Patent [19]

Weissman

[11] 4,205,443
[45] Jun. 3, 1980

[54] TWO-PART DOWEL PIN AND TOOL THEREFOR

[75] Inventor: Bernard Weissman, New York, N.Y.

[73] Assignee: IPCO Hospital Supply Corporation, White Plains, N.Y.

[21] Appl. No.: 903,744

[22] Filed: May 8, 1978

[51] Int. Cl.² .............................................. A61C 13/00
[52] U.S. Cl. ........................................................ 433/74
[58] Field of Search ..................... 32/11, 13, 40, 32, 71

[56] References Cited

U.S. PATENT DOCUMENTS

| | | | |
|---|---|---|---|
| 203,858 | 5/1878 | Starr | 32/40 R |
| 640,551 | 1/1900 | Fones | 32/13 |
| 1,279,805 | 9/1918 | Whitaker | 32/71 |
| 3,286,350 | 11/1966 | Cooper | 32/71 |
| 3,510,947 | 5/1970 | Tuccillo et al. | 32/32 |
| 3,518,761 | 7/1970 | Susman et al. | 32/11 |
| 3,521,354 | 7/1970 | Stern et al. | 32/11 |
| 3,932,939 | 1/1976 | Weissman | 32/11 |
| 4,054,995 | 10/1977 | Yoshida | 32/11 |

FOREIGN PATENT DOCUMENTS 2515445 10/1976 Fed. Rep. of Germany .............. 32/11

Primary Examiner—Louis G. Mancene
Assistant Examiner—John J. Wilson
Attorney, Agent, or Firm—Friedman, Goodman & Teitelbaum

[57] ABSTRACT

A dowel pin for removably mounting a dental model cast relative to a base cast, the dowel pin being a two-part structure to define a head portion and a shank portion extending therefrom, where the portions are threadedly engaged together in an axial alignment with each other. The head portion is adapted to be fixedly secured in the dental model cast so that the exposed end thereof is flush with a flat surface of the dental model cast. The shank portion is adapted to be removably insertable into a complimentary opening provided in the base cast, preferably with a sleeve member being provided in the opening to slidably receive the shank portion therein. The portions are selectively engageable and disengageable from each other whether or not the model cast is mounted upon the base cast. Accordingly, the dental model cast can easily be cut into segments after the head portion is secured therein. A tool is provided for engaging a free end of the shank portion in order to unthread the shank portion from the head portion so that the dental model cast or segments thereof can easily be removed from the base cast after the portions are disengaged.

18 Claims, 13 Drawing Figures

TWO-PART DOWEL PIN AND TOOL THEREFOR

BACKGROUND OF THE INVENTION

The present invention generally relates to prosthodontic casts, and more particularly to a two-part dowel pin which permits a simple separation and replacement of a dental model cast or segments thereof on a base cast.

Various dowel pins for permitting the separation and replacement of segments of a dental model cast on a base cast are already known in the prior art. Such dowel pins are shown in the Applicant's own U.S. Pat. Nos. 3,875,665 and 3,932,939, to which reference should be made. However, the dowel pins disclosed in the above mentioned patents, and also in the prior art, have a one piece construction. Accordingly, when removing the dental model segment, the dental model segment must be held firmly and usually wiggled in order to remove the prior art dowel pins from their associated sleeves in the base cast, thereby requiring a force to be placed upon the dental model segment which could cause damage to both the segment being removed and segments adjacent thereto.

Additionally, if the shank of the prior art dowel pin is damaged in some way, there is no convenient way of replacing the dowel pin in the segment without causing damage to the segment because the entire prior art dowel pins are fixedly secured in the segment.

Furthermore, it is difficult to cut the dental model cast into segments when the shanks of the prior art dowel pins are extending outwardly therefrom.

SUMMARY OF THE INVENTION

Accordingly, it is an object of the present invention to provide a pin arrangement for prosthodontic casts which overcomes the disadvantages of the prior art.

It is another object of the present invention to provide a two-part dowel pin which is simple in construction and economical to manufacture.

It is still another object of the present invention to provide a two-part dowel pin having a head portion threadedly engaged with a shank portion in an axial alignment with each other.

It is a further object of the present invention to provide a two-part dowel pin as described above which simplifies the removal of a segment of a dental model cast from a base cast.

It is yet a further object of the present invention to provide a two-part dowel pin which facilitates the cutting of a dental model cast into segments.

An added object of the present invention is to provide a tool for unthreading the shank portion of a two-part dowel pin as described above from the head portion thereof, whereby the head portion is fixedly secured in the dental model cast.

It is yet an additional object of the present invention to provide a method of mounting pins on a dental model cast or segments thereof for removal and replacement on a base cast.

In order to achieve the above objects, the present invention includes a dowel pin for removably mounting a dental model cast relative to a base cast, wherein the dowel pin is a two-part construction having a head portion and a shank portion extending therefrom, and thread means on the portions for disengageably securing the portions in axial alignment to each other. The head portion is adapted to be fixedly secured in the dental model cast and the shank portion is adapted to be removably insertable in a complimentary opening provided in the base cast, preferably with a sleeve member being provided in the opening to slidably receive the shank portion therein. Thus, the portions are selectively engageable and disengageable from each other whether or not the dental model cast is mounted upon the base cast.

According to this construction, the dental model cast can easily be cut into segments after the head portions are secured therein. Furthermore, a tool is provided for receiving a free end of the shank portion therein in order to unthread the shank portion from the head portion, whereby the dental model cast or segments thereof can easily be removed from the base cast after the portions are unthreaded from each other, whereby the shank portions are not required to be pulled through their associated sleeve members when the segments are removed. It is noted, that each segment of the dental model cast may be provided with two dowel pins of the present invention, or with a single dowel pin of the present invention preferably being associated with a similar type of dowel pin which may have a shorter shank portion.

BRIEF DESCRIPTION OF THE DRAWINGS

With the above and additional objects and advantages in view, as will hereinafter appear, this invention comprises the devices, combinations and arrangements of parts hereinafter described by way of example and illustrated in the accompanying drawings of a preferred embodiment in which.

DETAILED DESCRIPTION OF THE PREFERRED EMBODIMENT

Figure 1:
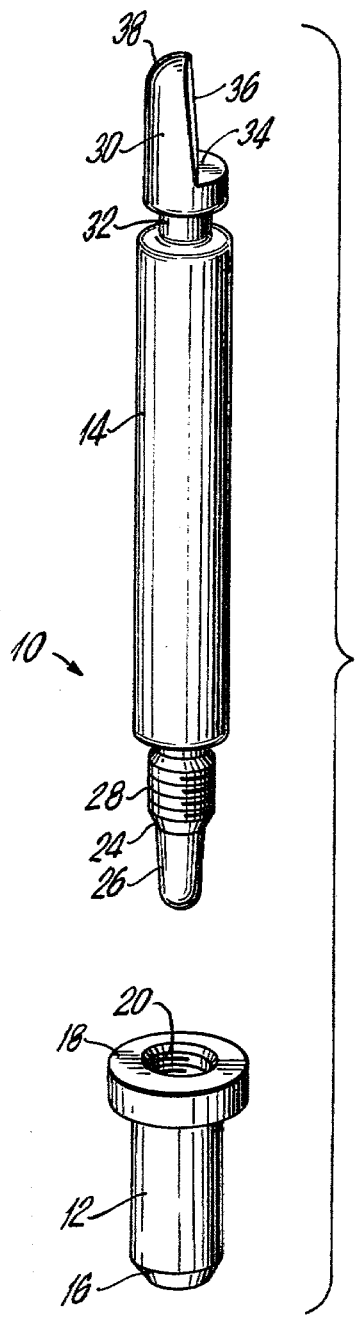
FIG. 1 is an exploded perspective view of the two-part dowel pin in accordance with the present invention.
Figure 3:
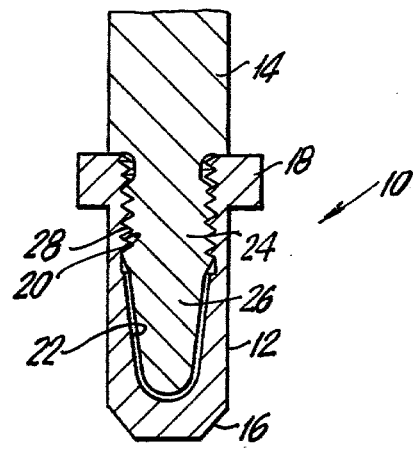
FIG. 3 is a fragmented cross-sectional view showing the threaded engagement between the head and shank portions of the dowel pin.

Referring now to the drawings, in which the same reference numerals are utilized to designate similar or identical parts throughout, FIG. 1 shows the two-part dowel pin 10 of the present invention. The dowel pin 10 includes a head portion 12 and a shank portion 14. The head portion 12 has a chamfer 16 at one end and an enlarged collar 18 at the opposite end thereof. An internal thread 20 is provided through the collar 18 and extends into the body of the head portion 12. As best shown in FIG. 3, a tapered opening 22 is provided within the head portion 12, the opening 22 being disposed inwardly of the thread 20, the function of which will be described hereinafter below.

The shank portion 14 is provided with a tip 24 having a reduced cross-section. The tip 24 includes a tapered pilot end 26 and an external thread 28 which is disposed inwardly from the pilot end 26. Thus, as shown in FIG. 3, the pilot end 26 of the shank portion 14 guides the tip 24 into the head portion 12 and is received in the tapered opening 22 as the thread 28 engages with the thread 20. Once the body of the shank portion 14 abuts against the collar 18 of the head portion 12, the portions 12, 14 are threadedly engaged as a unit.

Figure 2:
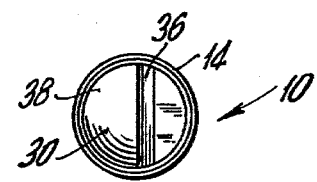
FIG. 2 is a top plan view of the dowel pin.
Figure 6:
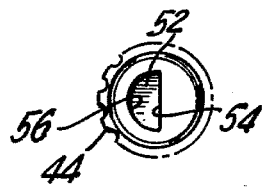
FIG. 6 is a fragmented sectional view showing the engagement between the tool and the shank portion.
Figure 6:
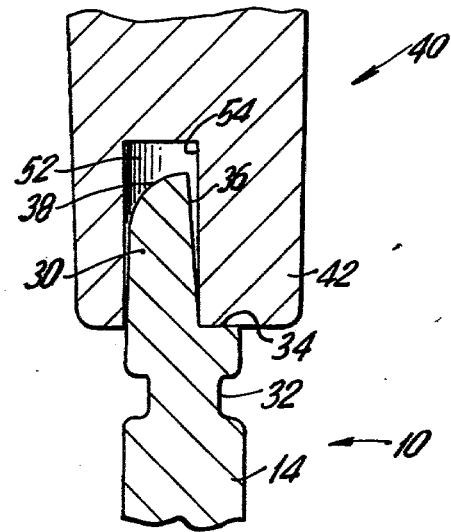

The opposite end of the shank portion 14 is provided with a manipulating end 30. The manipulating end 30 is spaced from the body of the shank portion 14 by an undercut or recess 32, the function of which will be discussed more fully below. The manipulating end 30 includes a recessed step 34 therein to provide a flat surface 36. The flat surface 36 is preferably tapered, to provide a thinner cross-section at its free end as best shown in FIGS. 2 and 6. The side 38 opposite the flat surface 36 is rounded, where the function of the flat surface 36 and the rounded surface 38 will be set forth hereinafter below.

Figure 4:
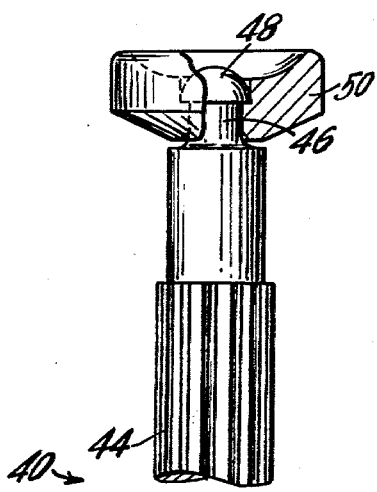
FIG. 4 is a fragmented perspective view, partly in section, of a tool for unthreading the shank portion from the head portion.

FIG. 4 shows a tool 40 for unthreading into shank portion 14 from the head portion 12. The tool 40 is constructed for manual holding thereof, and includes a cylindrical body member 42, which is preferably serrated or knurled at 44 for finger gripping thereof. A pin 46 with an enlarged arcuate head 48 extends centrally outwardly from the top of the body member 42 for rotatably holding a finger positioner disk 50 thereon.

Figure 5:
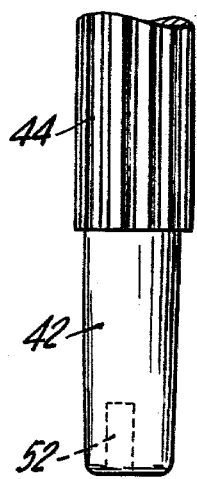
FIG. 5 is a bottom plan view of the tool.

The opposite end of the body member 42 is provided with an opening 52 therein. The opening 52 has a flat wall 54 and an arcuate wall 56 as best shown in FIG. 5, to define a half moon configuration. The opening 52 is configurated to receive the manipulating end 30 of the shank portion 14 therein as best shown in FIG. 6. Accordingly, the rounded surface 38 of the manipulating end 30 aids in inserting the manipulating end 30 into the opening 52, where the flat surface 36 of the manipulating end 30 is aligned side-by-side with the flat wall 54 of the opening 52. Additionally, the tapering of the flat surface 36 also aids in inserting and removing the manipulating end 30 from the opening 52 so that there is no tight engagement therebetween. Once the tool 40 receives the manipulating end 30 therein, with the body member 42 abutting against the recessed step 34, as shown in FIG. 6, any turning or rotation of the body member 42 will cause the flat wall 54 to turn or rotate the flat surface 36, so that the shank portion 14 rotates together with the body member 42 of the tool 40. Thus, by using the tool 40, the shank portion 14 can easily be unthreaded from the head portion 12, the purpose of which will be more fully discussed hereinafter below.

Figure 7:
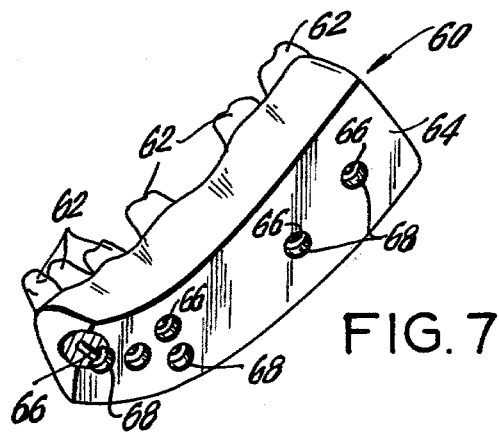
FIG. 7 is a perspective view, partly in section, of a dental model cast.

FIG. 7 shows a positive cast or a dental model cast 60 which is formed from an impression tray in accordance with techniques well known in the art. The dental model cast 60 is formed with tooth impressions 62 on one side thereof, where the opposite underside 64 is provided with a substantially flat surface. Accordingly, holes 66 are drilled into the flat underside 64 and are provided with countersinks 68. Preferably, there are two holes 66 for each anticipated segment which is to be cut from the dental model cast 60, as described in the above mentioned U.S. Pat. No. 3,932,939, to which reference should be made for a fuller description thereof.

Figure 8:
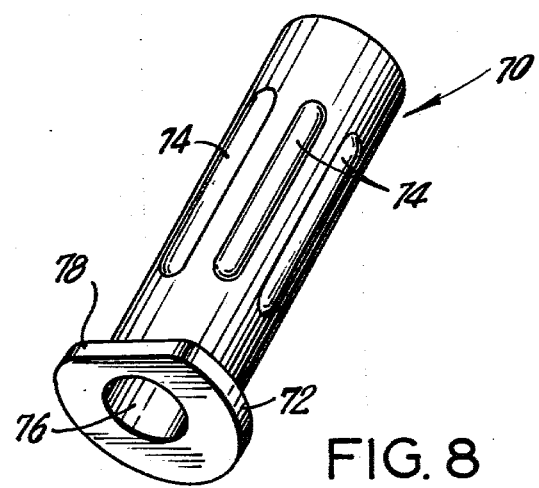
FIG. 8 is a perspective view of a sleeve member for receiving the shank portion therein.

FIG. 8 shows a tubular sleeve or bushing 70 which receives the shank portion 14. The sleeve 70 is provided with an annular shoulder 72 at one free end thereof which is substantially planar and extends in a radial direction. The body of the sleeve 70 is provided with elongated external ribs 74 which extend in a longitudinal direction, in the same direction as the opening 76 which extends longitudinally through the sleeve 70. Additionally, the annular shoulder 72 is provided with a cutaway edge portion 78. Both the ribs 74 and the cutaway edge portion 78 function to retain the sleeve 70 in a base cast, where the ribs 74 prevent the sleeve from being pulled out of the base cast, and also prevent rotation of the sleeve in the base cast. The cutaway edge portion 78 provides an additional feature to prevent rotation of the sleeve 70 in the base cast, where the formation of the base cast will be described hereinafter below.

Figure 9:
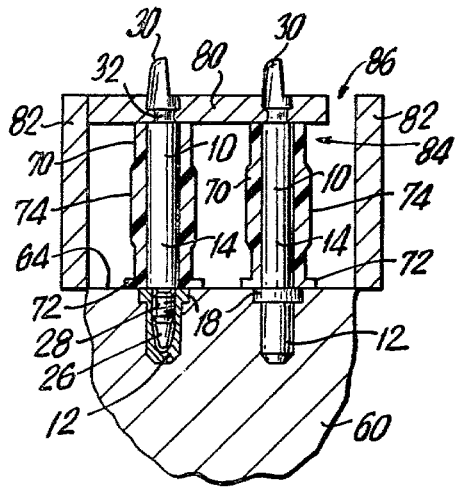
FIG. 9 is a cross-sectional view of the dental model cast having dowel pins therein and provided with wax sheets in preparation for the forming of the base cast.

As shown in FIG. 9, the first step in preparing the base cast is to fixedly secure the head portions 12 in the holes 66 in the flat surface 64 of the dental model cast 60 preferably by adhesive or cement means well known in the art. Accordingly, the collar 18 of the head portion 12 is received in the countersink 68 so that the exposed end surface of the collar 18 is in flush alignment with the flat surface 64 of the dental model cast 60. After the securement of the head portion 12, the shank portion 14 is threadedly engaged therewith, and the sleeve 70 is positioned on the shank portion 14 so that the annular shoulder 72 is positioned adajcent to the flat surface 64 of the dental model cast 60 as shown in FIG. 9.

A wax sheet 80 is disposed over the manipulating ends 30 of the dowel pins 10 and rests against the opposite ends of the sleeves 70 to be substantially parallel to the flat surface 64 of the dental model cast 60. Preferably, the manipulating ends 30 extend outwardly from the wax sheet 80 as shown in FIG. 9, where the walls of the apertures formed in the wax sheet 80 fit tightly around the undercut 32 of the shank portion 14. Further wax sheet walls 82 are disposed about the periphery of the flat surface 64 to form a dam or substantially vertical walls which, together with the wax sheet 80, define a substantially closed space 84. Accordingly, the wax sheet 80 is selected to be somewhat smaller than the flat surface 64 to thereby provide at least one space or opening 86 to permit access into the interior of the space 84.

Figure 10:
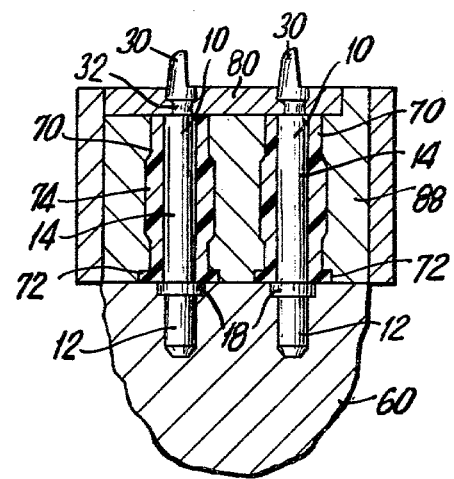
FIG. 10 is similar to FIG. 9 and shows a plaster base cast formed on the dental model cast.

With the above arrangement, a conventional plaster or any other suitable material utilized for this purpose can be poured into the space 84 through the access opening 86. Thus, as shown in FIG. 10, the sleeves 70 are embedded within the plaster which defines the base cast 88. It is noted, that the plaster does not physically come into contact with any of the dowel pins 10, so that the dowel pins 10 are free to slidably move or extend through the sleeves 70.

Figure 11:
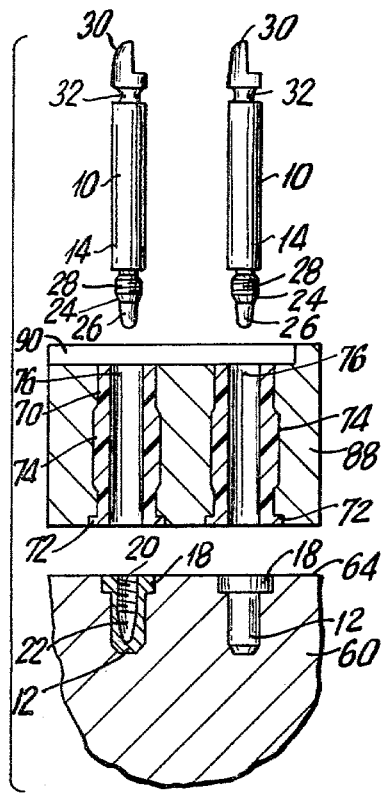
FIG. 11 is an exploded view, partly in section, showing the shank portions of the dowel pins removed from the base cast and separated from the head portions which are secured in the dental model cast.

After the plaster or base cast 88 has hardened, the wax sheets or walls 80, 82 are removed as shown in FIG. 11. To prevent any adhesion between the base cast 88 and the dental model cast 60, any suitable lubricant may be provided on the flat surface 64 prior to the pouring of the plaster. In this manner, the base cast 88 can be removed or separated from the dental model cast 60 without any great effort. It is noted, that the removal of the wax sheet 80 forms a recess 90 in the surface of the base cast 88.

The hardened base cast 88 can now be removed from the dental model cast 60 to provide the separated parts as shown in FIG. 11. The first step is to unthread the shank portion 14 from the head portion 12, using the tool 40 as mentioned above, whereby the tool 40 has easy access to receive the manipulating end 30 therein for the required rotation thereof.

After the shank portion 14 is unthreaded, the shank portion 14 is preferably pulled out of the sleeve 70 which is secured to the base cast 88, where this operation can be performed before or after the dental model cast 60 is removed. To facilitate the removal of the shank portion 14, a conventional tool (not shown) having a forked prong can be used whereby the forked prong is engaged in the undercut 32 in order to lift the shank portion 14 out of the sleeve 70. However, it is noted, that the shank portions 14 can also be pulled out by hand.

Once the shank portions 14 are unthreaded, whether or not they are removed from the sleeve 70, the base cast 88 can easily be lifted off the dental model cast 60, where there is no connection therebetween. It is noted, that the head portions 12 remain secured in the dental model cast 60.

Figure 12:
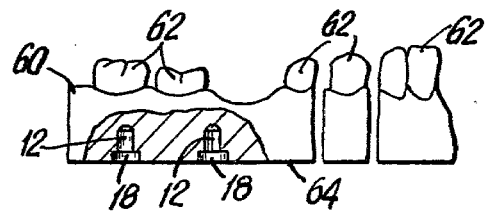
FIG. 12 is an elevational view, partly in section, showing the dental model cast cut in segments.

If desired, the dental model cast 60 may now be cut into segments, as shown in FIG. 12. Preferably, at least two head portions 12 are disposed in each segment for receiving associated shank portions 14, whereby two dowel pins 10 will hold and retain a segment on the base cast 88 in its original position so that the dentist can perform the required work thereon. According to the present invention, the flat surface 64 of the dental model cast 60 can be placed flat on a planar surface in order to cut the dental model cast 60 into the required segments, where the collars 18 are flush with the flat surface 64 and therefore do not interfere with the cutting process.

Figure 13:
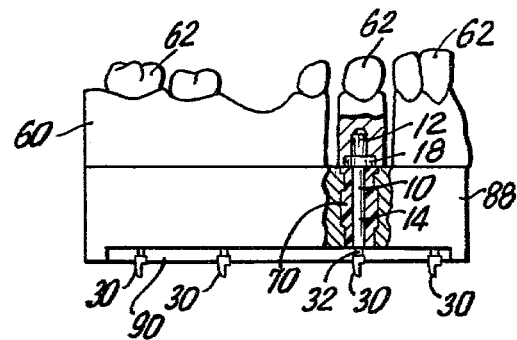
FIG. 13 is an elevational view, partly in section, showing the dowel pins positioning segments of the dental model cast on the base cast.

Once the dental model cast 60 is cut into segments, these segments can be replaced and removed easily from the base cast 88 as shown in FIG. 13. Preferably, when replacing a segment, the shank portions 14 are again threaded into the head portions 12, and the manipulating end 30 of the shank portion 14 is guided into the associated sleeves 70 provided therefor in the base cast 88. Here again, the rounded surface 38 aids in inserting the shank portion 14 into the collar 72 of its associated sleeve 70. The shank portions 14 are pushed into the sleeves 70 until the flat surface 64 of the segment abuts against the base cast 88, at which time the manipulating end 30 will extend out of the base cast 88 into the recess 90 as shown.

It is noted, that when the segment is again desired to be removed, the shank portion 14 is again unthreaded from the head portion 12 and the above mentioned process for removal thereof is repeated.

It is further noted, that the shank portions 14 are interchangeable whereby broken, bent or otherwise damaged shank portions 14 can easily be replaced.

It is further noted, that no significant force is exerted on any of the segments during removal thereof from the base cast 88, whereby the segments are merely lifted off the base cast 88 once the shank portions 14 are unthreaded.

Numerous alterations of the structure herein disclosed will suggest themselves to those skilled in the art. However, it is to be understood that the present disclosure relates to a preferred embodiment of the invention which is for purposes of illustration only and is not to be construed as a limitation of the invention.

What is claimed is:

1. A dowel pin for removably mounting a dental model cast relative to a base cast, said dowel pin comprising a head portion and a shank portion extending therefrom, engagement means provided on said portions for disengageably securing said portions in axial alignment to each other, said head portion being adapted to be fixedly secured in the dental model cast and said shank portion being adapted to be removably insertable into a complimentary opening provided in the base cast, said engagement means permitting said portions to be selectively engageable and disengageable from each other when the dental model cast is mounted upon the base cast, and also when the dental model cast and the base cast are separated, said engagement means including cooperating threads provided on said head and shank portions of said pin, said threads on one of said portions being externally disposed to define a male member, said threads on the other portion being internally disposed to define a female member for receiving said male member therein, and a free end of said male member being unthreaded to provide a pilot portion for guiding said male member into said female member.

2. A dowel pin as claimed in claim 1, wherein said one of said portions is said shank portion, and said other portion is said head portion.

3. A dowel pin as claimed in claim 1, wherein said head portion of said pin includes an enlarged collar portion at a free end thereof adapted to be positioned flush with an outer flat surface of the dental model cast.

4. A dowel pin as claimed in claim 1, wherein said engagement means are disposed at one end of said shank portion of said pin, and manipulating means are disposed at an opposite end of said shank portion of said pin for moving said shank portion relative to said head portion to unfasten said shank portion from said head portion.

5. A dowel pin as claimed in claim 4, wherein said manipulating means includes a flat surface longitudinally extending inwardly from a free end of said opposite end of said shank portion of said pin for turning said shank portion relative to said head portion.

6. A dowel pin as claimed in claim 5, wherein said flat surface on said opposite end of said shank portion is tapered to provide a greater cross-section inwardly from said free end thereof.

7. A dowel pin as claimed in claim 5, wherein said free end of said opposite end of said shank portion is rounded on an opposite side from said flat surface.

8. A dowel pin as claimed in claim 4, in combination with a tool for moving said manipulating means to unfasten said shank portion from said head portion.

9. A dowel pin in combination with a tool as claimed in claim 8, wherein said manipulating means includes a flat surface at a free end thereof, and said tool includes an aperture in one end thereof for receiving said free end of said manipulating means therein, said tool aperture including a flat wall positionable against said flat surface of said manipulating means for turning said manipulating means.

10. A dowel pin in combination with a tool as claimed in claim 9, wherein an opposite end of said tool is provided with a rotatably mounted finger positioner disk to aid in turning said tool, and a body portion of said tool being knurled for finger gripping thereof.

11. A dowel pin as claimed in claim 1, in combination with a sleeve member, said sleeve member including means for securing said sleeve member in the base cast, said sleeve member including an opening therethrough for removably receiving said shank portion of said pin in a sliding relationship therebetween.

12. A method of providing a pin on at least a segment of a dental model cast for removably mounting the segment of the dental model cast on a base cast, said method comprising:
   forming said pin in two pieces to provide a head portion and a shank portion which are disengageably securable together;
   securing said head portion in the segment of the dental model cast;
   providing an opening in the base cast to removably receive said shank portion for alignment with said head portion;
   joining said shank portion to said head portion with said shank portion extending outwardly from the segment of the dental model cast;
   placing said shank portion into said opening in the base cast to position the segment of the dental model cast against the base cast; and
   disengaging said shank portion from said head portion to remove the segment of the dental model cast from the base cast.

13. A method according to claim 12, wherein the step of joining said head and shank portions includes threading said shank portion into said head portion, and the step of disengaging said head and shank portions includes unthreading said shank portion from said head portion.

14. A method according to claim 13, wherein the step of unthreading said shank portion from said head portion includes inserting a free end of said shank portion into a tool, and turning said tool to rotate said shank portion relative to said head portion.

15. A method according to claim 12, wherein the step of securing said head portion in the segment of the dental model cast includes positioning a free end of said head portion in a flush relationship with an outer flat surface of the dental model cast.

16. A method according to claim 15, including the step of cutting the dental model cast into segments wherein each segment includes at least one head portion secured therein, the outer flat surface of the dental model cast being positioned on a planar surface during said cutting with said free end of said head portion being disposed adjacent to the planar surface.

17. A method according to claim 12, including providing a sleeve in said opening in the base cast for removably receiving said shank portion, said shank portion being slideably inserted into said sleeve.

18. A method according to claim 17, wherein the step of providing the sleeve includes securing said sleeve in said opening in the base cast with said sleeve extending from one side of the base cast to an opposite side thereof.

* * * * *